United States Patent [19]
Alfano et al.

[11] Patent Number: 5,644,429
[45] Date of Patent: *Jul. 1, 1997

[54] 2-DIMENSIONAL IMAGING OF TRANSLUCENT OBJECTS IN TURBID MEDIA

[75] Inventors: Robert R. Alfano, Bronx; Ping-Pei Ho, Great Neck; Xiangchun Liang, Bronx, all of N.Y.

[73] Assignee: Research Foundation of City College of New York, New York, N.Y.

[*] Notice: The term of this patent shall not extend beyond the expiration date of Pat. No. 5,371,368.

[21] Appl. No.: 654,800

[22] Filed: May 29, 1996

Related U.S. Application Data

[63] Continuation of Ser. No. 215,383, Mar. 21, 1994, abandoned, which is a continuation-in-part of Ser. No. 920,193, Jul. 23, 1992, Pat. No. 5,371,368.

[51] Int. Cl.$^6$ .................................................. G02B 27/46
[52] U.S. Cl. .......................................................... 359/559
[58] Field of Search ..................... 359/558, 559, 359/560, 561, 264; 372/12; 250/341.1, 358.1

[56] References Cited

U.S. PATENT DOCUMENTS

| | | | |
|---|---|---|---|
| 3,821,794 | 6/1974 | Yoneyama | 359/559 |
| 4,360,269 | 11/1982 | Iwamoto et al. | 359/559 |
| 4,381,137 | 4/1983 | Berg et al. | 359/559 |
| 4,389,092 | 6/1983 | Tamura | 359/559 |
| 5,140,463 | 8/1992 | Yoo et al. | |
| 5,142,372 | 8/1992 | Alfano et al. | |
| 5,227,912 | 7/1993 | Ho et al. | |
| 5,371,368 | 12/1994 | Alfano et al. | 250/341.1 |

OTHER PUBLICATIONS

Alfano et al., "Photons for prompt tumor detection," Physics World, pp. 37–40 (Jan. 1992).

Wang et al., "Ballistic 2–D Imaging Through Scattering Walls Using an Ultrafast Optical Kerr Gate," Science, vol. 253, pp. 769–771 (Aug. 16, 1991).

Wang et al., "Kerr–Fourier imaging of hidden objects in thick turbid media," Optics Letters, vol. 18, No. 3, pp. 241–243 (Feb. 1, 1993).

Duguay et al., "Ultrahigh Speed Photography of Picosecond Light Pulses and Echoes," Applied Optics, vol. 10, No. 9, pp. 2162–2170 (Sep. 1971).

Yoo et al., "Imaging of a translucent object hidden in a highly scattering medium from the early portion of the diffuse component of a transmitted ultrafast laser pulse," Optics Letters, vol. 17, No. 13, pp. 958–960 (Jul. 1, 1992).

*Primary Examiner*—Jon W. Henry
*Attorney, Agent, or Firm*—Kriegsman & Kriegsman

[57] ABSTRACT

A method of forming 2 dimensional image of a translucent object in or behind a turbid medium. In one embodiment, the method comprises the steps of illuminating the translucent object through one side of the turbid medium with an ultrafast pulse of light, the light emergent from the opposite side of the turbid medium consisting of a ballistic component, a snake-like component and a diffuse component. The emergent light is then temporally and spatially gated to preferentially pass the ballistic component and the snake-like component. Preferably, the temporal and spatial gating is achieved by positioning the Kerr cell of an optical Kerr gate at the 2F spectral plane of a 4F Kerr-Fourier imaging system. At the appropriate time, that portion of the Kerr cell located at the focal point of the 2F spectral plane is gated open, allowing predominantly ballistic and snake-like components of the transilluminated light to pass therethrough. A cooled CCD detector is positioned at the 4F spectral plane to form a 2-dimensional image of the temporally and spatially gated light.

3 Claims, 5 Drawing Sheets

2-DIMENSIONAL IMAGING OF TRANSLUCENT OBJECTS IN TURBID MEDIA

The present application is a continuation of U.S. patent application Ser. No. 08/215,383, filed Mar. 21, 1994, now abandoned, which in turn is a continuation-in-part of U.S. patent application Ser. No. 07/920,193, filed Jul. 23, 1992, now U.S. Pat. No. 5,371,368.

BACKGROUND OF THE INVENTION

The present invention relates generally to the imaging of objects in turbid media and more particularly to the imaging of translucent objects in turbid media.

As can readily be appreciated, there are many situations in which the detection of an object hidden in a turbid, i.e., highly scattering, medium is highly desirable. For instance, the detection of a tumor embedded within a tissue is one such example. Although x-ray techniques do provide some measure of success in detecting objects in turbid media, they are not well-suited for detecting very small objects, e.g., tumors less than 1 mm in size, or for detecting objects in thick media. In addition, x-ray radiation can present safety hazards to a person exposed thereto.

An alternative technique used to detect objects in turbid media is transillumination. In transillumination, visible light is incident on one side of a medium and the light emergent from the opposite side of the medium is used to form an image. Objects embedded in the medium typically absorb the incident light and appear in the image as shadows. Unfortunately, the usefulness of transillumination as a detection technique is severely limited in those instances in which the medium is thick or the object is very small. This is because light scattering within the medium contributes to noise and reduces the intensity of the unscattered light used to form the image shadow.

To improve the detectability of small objects located in or behind a turbid medium using transillumination, one must separate the unscattered light from the scattered light. This may be done by exploiting the properties of photon migration through a scattering medium. When photons migrate through a turbid medium, they can be categorized into three main signal components: (1) the ballistic (coherent, forward-scattered) photons which arrive first by traveling over the shortest, most direct path; (2) the snake (quasicoherent) photons which arrive within the first $\delta t$ after the ballistic photons and which deviate, to a small extent, off a straight-line propagation path; and (3) the diffusive (incoherent) photons which, due to a great deal of scattering within the medium, deviate considerably from a straight-line propagation path. Because they travel over a much larger distance than the ballistic or snake photons, the diffusive photons take the longest amount of time to traverse the medium. It is believed that the ballistic and snake components contain the least distorted image information and that the diffusive component loses most of the image information.

Therefore, to make transillumination work most effectively with turbid media, one should selectively detect the ballistic and snake-like photons, which contain valuable information about the object, and reject diffuse photons, which only contribute noise. This process of selection and rejection has been implemented in various time-gating, space-gating and time/space-gating techniques. Patents, patent applications and publications which disclose certain of these techniques include U.S. Pat. No. 5,140,463, inventors Yoo et al., which issued Aug. 18, 1992; U.S. Pat. No. 5,142,372, inventors Alfano et al., which issued Aug. 25, 1992; U.S. Pat. No. 5,227,912, inventors Ho et al., which issued Jul. 13, 1993; presently-pending and allowed U.S. patent application Ser. No. 07/920,193, inventors Alfano et al., filed Jul. 23, 1992; Alfano et al., "Photons for prompt tumor detection," *Physics World*, pp. 37–40 (January 1992); Wang et al., "Ballistic 2-D Imaging Through Scattering Walls Using an Ultrafast Optical Kerr Gate," *Science*, Vol. 253, pp. 769–771 (Aug. 16, 1991); and Wang et al., "Kerr-Fourier imaging of hidden objects in thick turbid media," *Optics Letters*, Vol. 18, No. 3, pp. 241–243 (Feb. 1, 1993), all of which are incorporated herein by reference.

Of the above art, Wang et al., "Kerr-Fourier imaging of hidden objects in thick turbid media," *Optics Letters*, Vol. 18, No. 3, pp. 241–243 (Feb. 1, 1993) is illustrative. In this article, there is disclosed a time/space-gating system for use in imaging opaque test bars hidden inside a 5.5 cm-thick 2.5% Intralipid solution. The disclosed system includes three main parts: a laser source, an optical Kerr gate and a detector. The laser source is a picosecond mode-locked laser system, which emits a 1054 nm, 8 ps laser pulse train as the illumination source. The second harmonic of the pulse train, which is generated by transmission through a potassium dihydrate phosphate (KDP) crystal, is used as the gating source. The illumination source is sent through a variable time-delay and is then used to transilluminate, from one side, the turbid medium containing the opaque object. The signal from the turbid medium located at the front focal plane of a lens is collected and transformed to a Kerr cell located at its back focal plane (i.e., the Fourier-transform spectrum plane of a 4F system). That portion of the Kerr cell located at the focal point of the 4F system is gated at the appropriate time using the gating source so that only the ballistic and snake components are permitted to pass therethrough. The spatial-filtered and temporal-segmented signal is then imaged by a second lens onto a CCD camera.

It should be noted that none of the art mentioned above is directed specifically to the imaging of translucent, as opposed to opaque, objects in turbid media. The distinction between translucent and opaque objects is believed to be significant in the field of transillumination since opaque objects absorb transilluminated light whereas translucent objects scatter transilluminated light.

One reference which does relate specifically to the imaging of translucent objects in turbid media is Yoo et al., "Imaging of a translucent object hidden in a highly scattering medium from the early portion of the diffuse component of a transmitted ultrafast laser pulse," *Optics Letters*, Vol. 17, No. 13, pp. 958–960 (Jul. 1, 1992), which is incorporated herein by reference. In this paper, there is disclosed a time-resolved imaging setup which comprises a colliding-pulse, mode-locked dye laser whose output is focused by a long-focal-length lens into a 0.3 mm spot on the turbid medium. Two 1 mm diameter apertures spaced 0.5 m apart are placed on the opposite side of the turbid medium so as to permit only light traveling along the incident axis to be detected by a streak camera. A reference pulse is used to get the zero time for the temporal profile of the scattered pulse.

The aforementioned Yoo paper, however, does not teach or suggest using the light emergent from the turbid medium to form a 2-dimensional image of the translucent object in the turbid medium.

SUMMARY OF THE INVENTION

It is an object of the present invention to provide a new method for imaging a translucent object in or behind a turbid medium.

It is another object of the present invention to provide a method for obtaining a 2-dimensional image of a translucent object in or behind a turbid medium.

Additional objects, as well as features and advantages thereof, will be set forth in part in the description which follows, and in part will be obvious from the description or may be learned by practice of the invention. The objects of the invention also may be realized and attained by means of instrumentalities and combinations particularly pointed out in the appended claims.

In furtherance of the above and other objects, a method for obtaining a 2-dimensional image of a translucent object in or behind a turbid medium comprises, in one embodiment, the steps of: (a) illuminating the translucent object through the turbid medium with a pulse of light, the light emergent from the turbid medium consisting of a ballistic component, a snake-like component and a diffuse component; (b) temporally and spatially gating the emergent light to preferentially pass said ballistic component and said snake-like component; and (c) forming a 2-dimensional image of the translucent object in or behind the turbid medium using the temporally and spatially gated light.

Preferably, said temporally and spatially gating step is effected using a 4F Kerr-Fourier imaging system, said system including a Kerr cell located at the 2F spectral plane of the 4F system, with only that portion of the Kerr cell located at the focal point of the 2F plane being gated.

In another embodiment, a method for obtaining a 2-dimensional image of a translucent object in or behind a turbid medium comprises the steps of: (a) illuminating the translucent object through the turbid medium, the light emergent from the turbid medium consisting of a ballistic component, a snake-like component and a diffuse component; (b) spatially gating the emergent light to preferentially pass said ballistic component and said snake-like component; and (c) forming a 2-dimensional image of the translucent object in or behind the turbid medium using the spatially gated light.

Preferably, said spatially gating step is effected using a 4F Fourier imaging system, said system including an aperture placed at the focal point of the 2F spectral plane of the 4F system.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
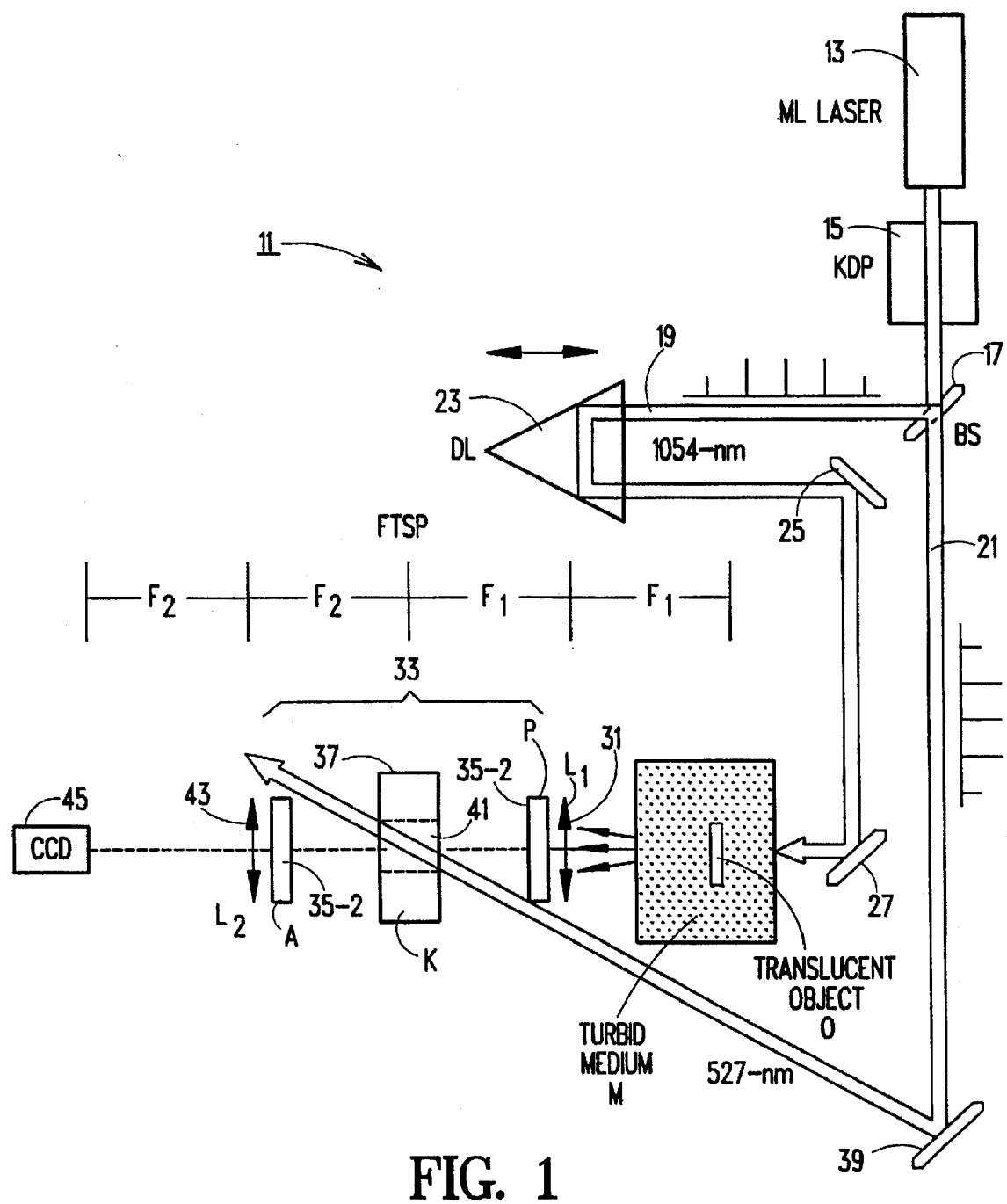
FIG. 1 is a schematic diagram of a system for obtaining a 2-dimensional image of translucent object in a turbid medium in accordance with one embodiment of the method of the present invention.

Referring now to FIG. 1, there is shown a schematic diagram of a system for obtaining a 2-dimensional image of a translucent object in a turbid medium in accordance with one embodiment of the method of the present invention, the system being represented generally by reference numeral 11.

System 11 includes a laser 13 which, in the present embodiment, is a single shot $Nd^+$:glass mode-locked laser used to generate a pulse train of 1054-nm, 8-ps pulses. A potassium dihydrate phosphate (KDP) crystal 15 is placed along the path of the output of laser 13 for generating a pulse train of second harmonic, 527-nm pulses. A dichroic beam splitter 17 is used to cause the 1054 nm pulses to propagate along an illumination path 19 and to cause the 527 nm pulses to propagate along a gating path 21. A movable-prism delay 23 and a pair of mirrors 25 and 27 are disposed along illumination path 19 to cause the 1054-nm pulse train to transilluminate, at the appropriate time, a turbid medium M containing a translucent object O.

The light emergent from the opposite side of turbid medium M is brought to focus by a first lens 31 having a focal length of 60 cm. A Kerr gate 33, comprising a pair of crossed calcite polarizers 35-1 and 35-2 and a 1-cm long $CS_2$ Kerr cell 37, is placed after lens 31, with Kerr cell 37 being positioned at the back focal plane of lens 31. A mirror 39 is disposed along gating path 21 so that the 527-nm pulses induce only that portion 41 of Kerr cell 37 located at the focal point of lens 31 to permit light to pass therethrough. A second lens 43 having a focal length of 27 cm is placed after Kerr gate 33, with Kerr cell 33 being located at its front focal plane and a cooled CCD camera 45, with 16-bit resolution and $2.5 \times 10^5$ detection pixels, being located at its back focal plane.

As can be seen, lenses 31 and 43, Kerr gate 33 and CCD 45 are all arranged in the form of a 4F imaging system, with Kerr gate 33 being located at the 2F spectral plane. Temporal filtering of diffuse light is achieved by the gating of Kerr cell to pass only early-arriving, i.e., ballistic and snake-like, light. Spatial filtering of diffuse light is achieved by the gating of only that portion of Kerr cell located at the focal point of lens 31.

Figure 2:
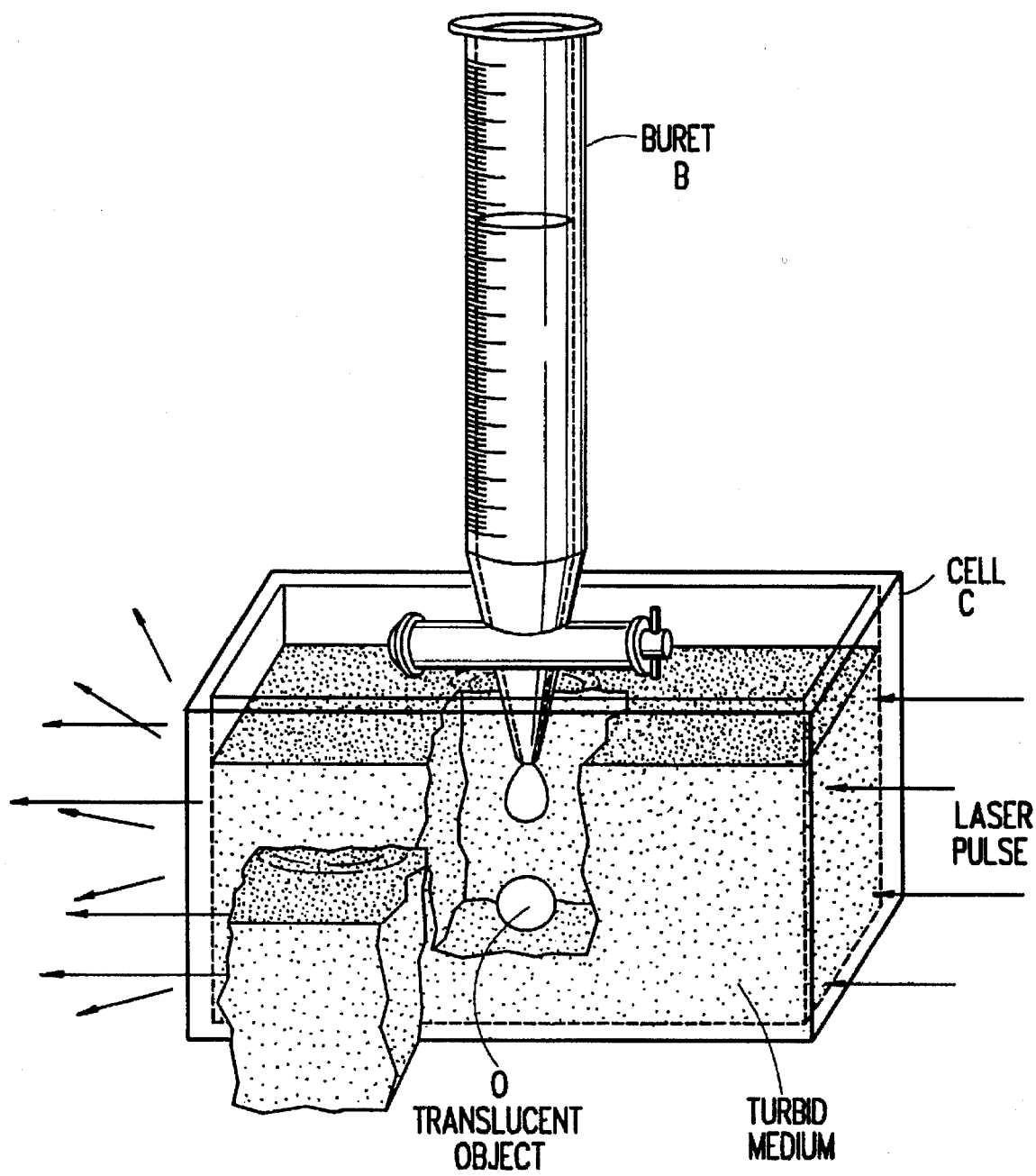
FIG. 2 is a schematic diagram of an experimental arrangement of a turbid medium containing droplets of a translucent liquid.

Referring now to FIG. 2, there is shown a schematic diagram of an experimental arrangement which may be used to obtain a translucent object O located within a turbid medium M for evaluation using system 11. The arrangement includes a cell C having inside dimensions of $50 \times 50 \times 50$ $mm^3$. A 2% diluted Intralipid stock solution of 10% Intralipid (the final solution therefore being 0.2% Intralipid) is contained within cell C and serves as the turbid medium. Translucent droplets of either pure water or a diluted Intralipid solution were dispensed into medium M using a 50 mL Kimex buret B having a straight bore stopcock with PTFE plug. The subdivision or the limit of error of buret B is 0.1 ml. The transport coefficients, $\mu_t$, of this modeled turbid medium at input wavelengths of 625 nm and 1060 nm are approximately 1/(2.4 mm) and 1/(5.0 mm), respectively. These scattering coefficients are similar to that of human breast tissue. The measured attenuation coefficient of this modeled turbid medium, using system 11, is 1/(2.6 mm). The absolute signal collected was about $10^{-10}$ from the input probe beam. The absorption length of the modeled Intralipid solution is on the order of 500 mm and can be neglected in our experimental arrangements.

Figure 3A:
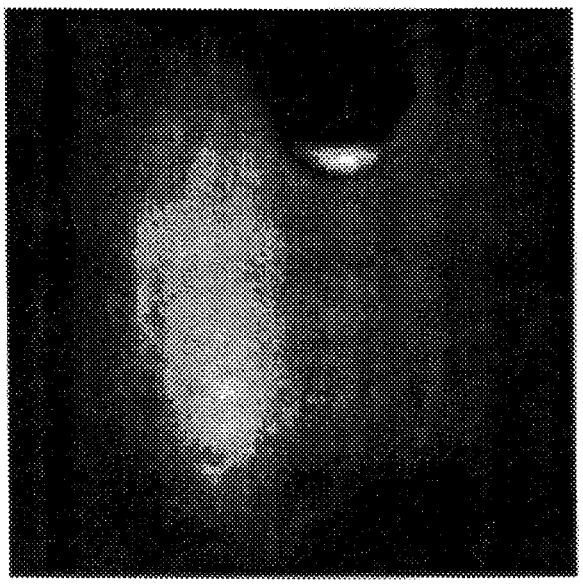
FIGS. 3(a) through 3(c) are 2-dimensional images of water droplets located inside a turbid medium obtained using the system of FIG. 1.
Figure 3B:
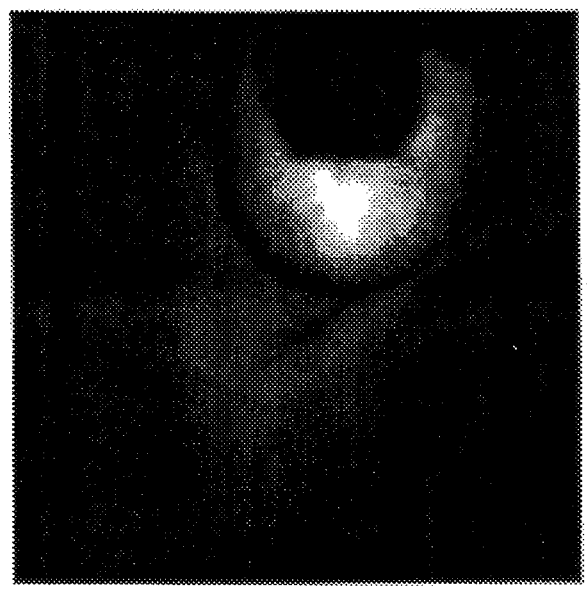
Figure 3C:

FIGS. 3(a) through 3(c) are 2-dimensional images, obtained using system 11, of a translucent water droplet situated inside a 50 mm thick 2% diluted Intralipid solution obtained using system 11. The shape and spatial distribution of the water droplet depends on the amount of water in the droplet and the delay of release time. The dark shadow at the top middle part of the white laser beam circle is the end tip of the buret. Since the scattering loss from the water droplet is less than that from the surrounding host, the intensity of the projected water droplet image was brighter. The inhomogeneity of the brighter circle in FIGS. 3(a) through 3(c) which corresponds to the collection aperture or signal beam diameter of about 12.7 mm is accounted for by the non-uniformity of the laser intensity distribution. In FIG. 3(a), the delay from releasing stopper is about 2 seconds whereas in FIGS. 3(b) and 3(c), the delay from releasing stopper is about 5 second and about 10 seconds, respectively.

Figure 4A:
FIGS. 4(a) through 4(d) are 2-dimensional images, obtained using the system of FIG. 1, of translucent 1%, 2%, 3% and 5%, respectively, diluted Intralipid-containing droplets situated inside a 50 mm thick 2% diluted Intralipid solution.
Figure 4B:
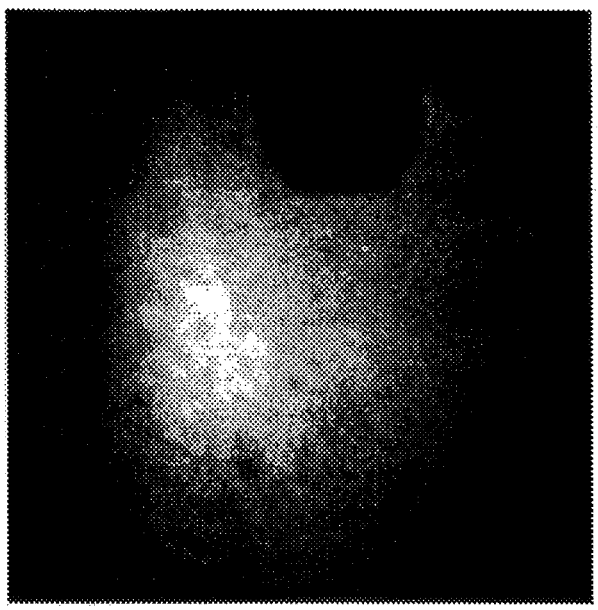
Figure 4C:
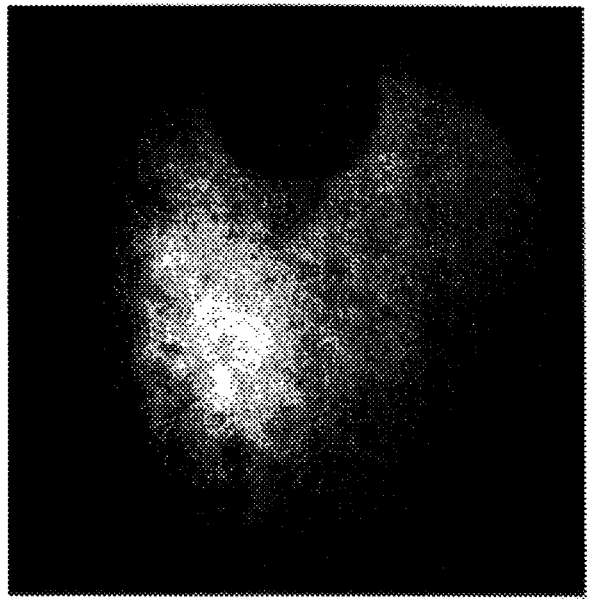
Figure 4D:
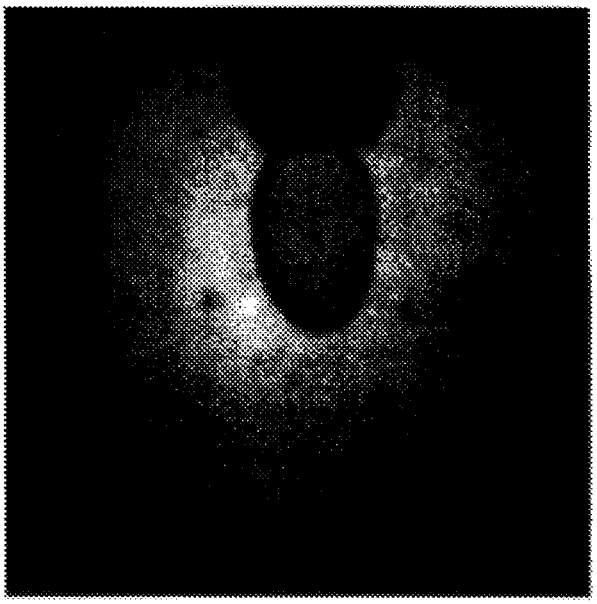

FIGS. 4(a) through 4(d) are 2-dimensional images, obtained using system 11, of various translucent Intralipid-containing droplets situated inside a 50 mm thick 2% diluted Intralipid solution. The droplets of FIGS. 4(a) through 4(d) are 1%, 2%, 3% and 5% diluted Intralipid solutions, respectively. The projected image from the 5% Intralipid droplet shown in FIG. 4(d) is the darkest due to the increasing of scattering from the droplet whereas the projected image from the 2% Intralipid droplet shown in FIG. 4(b) is hardly distinguishable from the surrounding host, which has an identical scattering property. The image obtained from the 1% Intralipid droplet shown in FIG. 4(a) is brighter than that from the 2% surrounding host, and the image from the 3% Intralipid droplet in FIG. 4(c) is darker. The foregoing suggests that a 1% concentration dilution difference between the droplet and the medium can be visually distinguished. The changes of the shape of the drop can also be measured. A much smaller concentration difference of 0.1% between the droplet and the medium could be identified using digital video signal processing. Accordingly, the present method can be used to obtain a 2-dimensional image of a first translucent medium in or behind a second translucent medium wherein the respective scattering coefficients of the two translucent media differ by at least about 0.1%.

Figure 5:
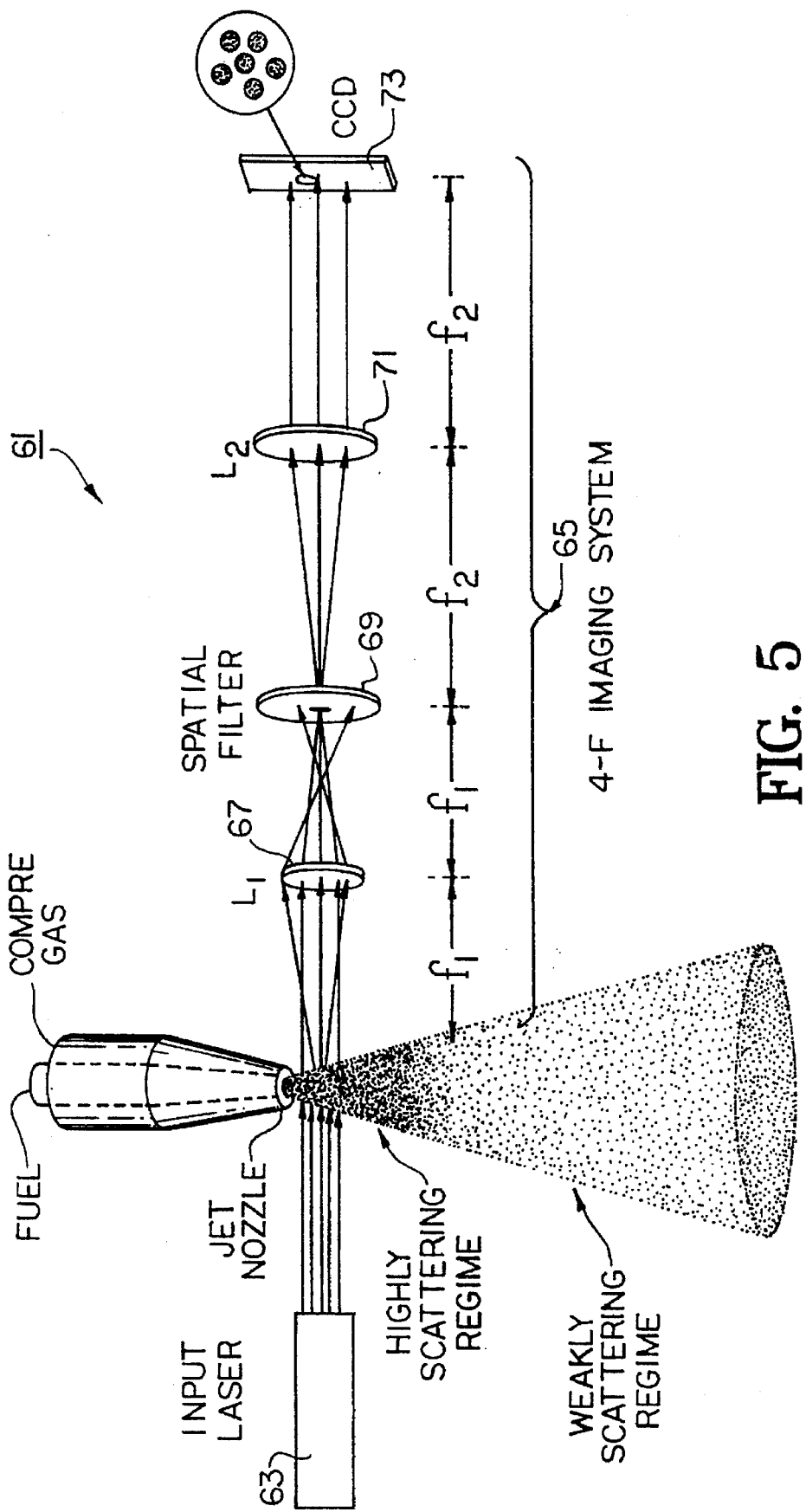
FIG. 5 is a schematic diagram of a system for obtaining a 2-dimensional image of a translucent object in a turbid medium in accordance with another embodiment of the method of the present invention.

Referring now to FIG. 5, there is shown a schematic diagram of a system for obtaining a 2-dimensional image of a translucent object in a turbid medium in accordance with another embodiment of the method of the present invention, the system being represented generally by reference numeral 61.

System 61 is considerably less complex than system 11 and does not use temporal and spatial gating to selectively filter the ballistic and snake-like components of the transilluminated light. Instead, system 61 relies exclusively on spatial gating to preferentially block out the diffuse component of the transilluminated light.

System 61, which in the embodiment shown is being used to image droplets of fuel in a jet stream, comprises a laser source 63. Laser source 63 may emit either a train of light pulses or a continuous wave for use in illuminating the turbid medium. The light emergent from the opposite side of the turbid medium is then imaged using a 4F imaging system 65. System 65 comprises a first lens 67, an aperture 69, a second lens 71 and a cooled CCD camera 73. Aperture 69 is centered at the back focal plane of lens 67 (the 2F spectral plane), and CCD 73 is positioned at the back focal plane of lens 71 (the 4F spectral plane).

Some possible uses or applications to which the method of the present invention may be put are as follows: (1) to diagnose diseases using time-gated imaging, e.g., breast cancer screening, cholesterol concentration in blood vessels in vivo, blood vessel clogging, oxygen concentration in blood vessels, gum disease, prostate cancer, etc.; (2) to image the spatial distribution of one fluid in another fluid; (3) to image drops inside another liquid; (4) to image the states of fluctuations of various turbid fluids; (5) to image the spatial distribution of particles and/or aggregates of particles in turbid fluids; (6) to diagnose silicone leakage from breast implantation; (7) to diagnose fluid distribution and ear pressure in cochlea; (8) to diagnose blood leakage in brain; (9) to diagnose oil spread in oil and/or other turbid environment; (10) to diagnose crystal defects and dislocations in crystals and semiconductors; and (11) to diagnose exhaust from engines and/or jet streams.

Additional possible uses, qualifications and/or variations to the method of the present invention are as follows: (1) use a fast processing/display (<0.05 seconds) and a slow processing/display (>0.1 seconds) video systems to image the ballistic/snake images. The fast display video system will provide a fast and rough image for the alignment and safety monitoring. The slow display video system will provide a long signal average for better sensitivity and accuracy. These two (slow and fast) imaging systems will obtain the transmitted ballistic/snake signals using optical beam splitter, mechanical mirror in and out, or electronic splitting from a video camera system; (2) use time-gated imaging technique to distinguish cancer tissues from normal tissues using the differences of water concentration; (3) use multiple (two or more) wavelengths in the wavelength region of 650 nm to 1500 nm and differential absorption cross-section to image the diseased tissues from the normal tissues, based on the concentrations of hemoglobin and water; (4) use Forsterite laser with tunable wavelengths from 1150 nm to 1350 nm and Cr:YAG laser from 1300 nm to 1550 nm to identify water concentration and use mode-locked Ti:sapphire laser with tunable wavelengths from 650 nm to 1000 nm to probe the concentrations of blood and other chromophores; (5) use spatial aperture to modify spatial frequency at the Fourier plane of the time-gate to further filter late diffusive noise and place time-gate at the Fourier plane to select and modify image spatial frequencies of the early ballistic/snake light; (6) use laser field induced optical apertures for a means of the spatial aperture made out of a pin hole from a metal plate; (7) use zoom lenses in the 4F Fourier imaging system to compensate for thickness variation of the sample; (8) use cooled 2D video detectors to image ballistic/snake signals from 250 nm to 1100; (9) use PtSi video detectors to image signals in the wavelength region of 1000 nm to 3000 nm; (10) use single ray scanning method to reconstruct the 3-D image from ballistic/snake signals; (11) use imaging disparity through angular displacement from two 2D ballistic/snake images to reconstruct 3D stereographic image; (12) use angular coding in sequence or in parallel to introduce image disparity for the 2D ballistic/snake images; (13) use sequential and/or parallel polarization coding to display snake 3D stereoscopic images; (14) use single coherent fiber bundle for single beam non-scanning illumination to acquire ballistic/snake images; (15) use video cassette recorder for massive analog 2D ballistic/snake image recording and storage; (16) use 2D coherent-fiber-CCD assembly for directly 2D and 3D time-gated ballistic imaging; and (17) use steady-state 4F imaging system for translucent objects inside scattering turbid objects.

The embodiments of the present invention are intended to be merely exemplary and those skilled in the art shall be able to make numerous variations and modifications to them without departing from the spirit of the present invention. All such variations and modifications are intended to be within the scope of the present invention as defined in the appended claims.

What is claimed is:

1. A method for obtaining a 2-dimensional image of a translucent object in or behind a turbid medium comprising the steps of:

(a) illuminating the translucent object through the turbid medium with a pulse of light, the light emergent from the turbid medium consisting of a ballistic component, a snake-like component and a diffuse component;

(b) simultaneously temporally and spatially gating the emergent light to preferentially pass said ballistic component and said snake-like component; and (c) forming a 2-dimensional image of the translucent object in or behind the turbid medium with the temporally and spatially gated light.

2. A method for obtaining a 2-dimensional image of a translucent object in or behind a turbid medium comprising the steps of:

(a) illuminating the translucent object through the turbid medium with a pulse of light, the light emergent from the turbid medium consisting of a ballistic component, a snake-like component and a diffuse component;

(b) temporally and spatially gating the emergent light to preferentially pass said ballistic component and said snake-like component wherein said temporally and spatially gating step is effected using a Kerr cell located at the 2F spectral plane of a 4F Kerr-Fourier imaging system, with only that portion of the Kerr cell located at the focal point of the 2F plane being gated; and (c) forming a 2-dimensional image of the translucent object in or behind the turbid medium using the temporally and spatially gated light.

3. A method for obtaining a 2-dimensional image of a first translucent medium in or behind a second translucent medium, said method comprising the steps of:

(a) illuminating the first translucent medium through the second translucent medium with a pulse of light, the light emergent from the second translucent medium consisting of a ballistic component, a snake-like component and a diffuse component;

(b) simultaneously temporally and spatially gating the emergent light to preferentially pass said ballistic component and said snake-like component; and (c) forming a 2-dimensional image of the first translucent medium in or behind the second translucent medium with the temporally and spatially gated light.

* * * * *